United States Patent [19]

Niedrach et al.

[11] Patent Number: 4,681,673

[45] Date of Patent: Jul. 21, 1987

[54] PORTABLE OXYGEN SENSOR WITH SHORTENED BREAK-IN TIME

[75] Inventors: Leonard W. Niedrach; Fritz G. Will, both of Schenectady, N.Y.

[73] Assignee: General Electric Company, Schenectady, N.Y.

[21] Appl. No.: 877,612

[22] Filed: Jun. 23, 1986

Related U.S. Application Data

[62] Division of Ser. No. 665,672, Oct. 29, 1984.

[51] Int. Cl.[4] .......................... G01N 27/46; B22F 3/12
[52] U.S. Cl. .................................. 204/415; 204/56.1; 204/96; 148/6.31; 148/432; 423/604; 264/61; 419/22
[58] Field of Search ...................... 204/56 R, 96, 415; 423/604; 419/22; 264/61; 148/432

[56] References Cited

U.S. PATENT DOCUMENTS

| | | | |
|---|---|---|---|
| 766,815 | 8/1904 | Edison | 429/220 |
| 1,523,029 | 1/1925 | Martus | 429/220 |
| 1,941,869 | 1/1934 | Martus et al. | 429/220 |
| 2,991,412 | 7/1961 | Kordesch | 204/432 |
| 3,149,921 | 9/1964 | Warner | 204/1 T |
| 3,616,411 | 10/1971 | Rudek et al. | 204/415 |
| 3,948,746 | 4/1976 | Poole | 204/415 |
| 4,132,616 | 1/1979 | Tantram et al. | 204/415 |
| 4,176,032 | 11/1979 | Stevenson | 204/415 |
| 4,524,115 | 6/1985 | Paulson et al. | 429/220 |

*Primary Examiner*—T. Tung
*Attorney, Agent, or Firm*—Paul E. Rochford; James C. Davis, Jr.; James Magee, Jr.

[57] ABSTRACT

An improved oxygen sensor is provided which gives oxygen concentration readings immediately and without the uncertain delays of a break-in period. The break-in period is decreased substantially by imparting to a copper counter electrode a uniform distribution of cuprous oxide throughout its structure. More reliable performance of the sensor is achieved.

9 Claims, 3 Drawing Figures

PORTABLE OXYGEN SENSOR WITH SHORTENED BREAK-IN TIME

This application is a division of application Ser. No. 665,672 filed Oct. 29, 1984.

BACKGROUND OF THE INVENTION

The present invention relates to oxygen sensors suitable for use in spacecraft and for other uses. More specifically, it relates to shortening the break-in time for the useful life of oxygen sensors such as are used on the space shuttle.

It has been observed that an oxygen sensor as illustrated in FIG. 1 has a total life of approximately 8000 hours when exposed to 1 atmosphere of air at 75° F. Total life includes both useful operating life and exposure to oxygen for testing, storage and for any other reason. The calculated total life of a sensor as illustrated in FIG. 1 is approximately 9200 hours. The original specifications of the National Aeronautics and Space Administration for such sensors is 6236 operational hours of useful operating life.

Because substantial initial break-in time as well as testing and operation of sensors is necessary prior to an actual mission, an appreciable portion of the total life of such a sensor is used up in the break-in period, in laboratory testing, in various calibrations and in an air exposure aboard the spacecraft before the scheduled launch. This can be further extended by delays in the actual launch thus using up a further portion of the total life of the sensor. In all, a significant fraction of the total life of the sensor is used in this way. For these and other reasons, reduced sensor output has mandated premature sensor replacement prior to a number of space shuttle missions. There is considerable interest in NASA in avoiding such operating complications in providing oxygen sensing in a spacecraft.

The term oxygen sensor as used herein includes an oxygen sensor cell such as is illustrated in FIG. 1 and electrical circuitry most of which is external to the cell and which is illustrated schematically in FIG. 2. An essential component of an oxygen sensor cell is a counter electrode one form of which is illustrated in FIG. 3.

BRIEF STATEMENT OF THE INVENTION

Accordingly, it is one object of the present invention to improve the design of oxygen sensor cells for space and other applications.

Another object is to provide a sensor capable of stable operation within a short time of assembly.

Another object is to provide an oxygen sensor having a shortened break-in time.

Another object is to provide an oxygen sensor having a useful life which does not require uncertain and extended break-in.

Another object is to provide an oxygen sensor for space applications which has a more clearly determinable start of its useful life.

Another object is to provide an oxygen sensor cell which is storable.

Still another object is to provide a storable oxygen sensor the operation of which can be initiated by introduction of alkaline electrolyte there into.

Other objects and advantages of the present invention will be, in part, apparent and, in part, pointed out in the description which follows.

In one of its broader aspects, objects of the present invention may be achieved by providing a body of copper of relatively high porosity, distributing cuprous oxide uniformly through said porous body to the extent of 0.1 to 5 percent by weight, maintaining the porosity before operation of said body at at least 15 percent by volume and incorporating the body as a counter electrode in an oxygen sensor cell.

BRIEF DESCRIPTION OF THE DRAWINGS

The description which follows will be better understood by reference to the accompanying drawings in which.

DETAILED DESCRIPTION OF THE INVENTION

Figure 1:
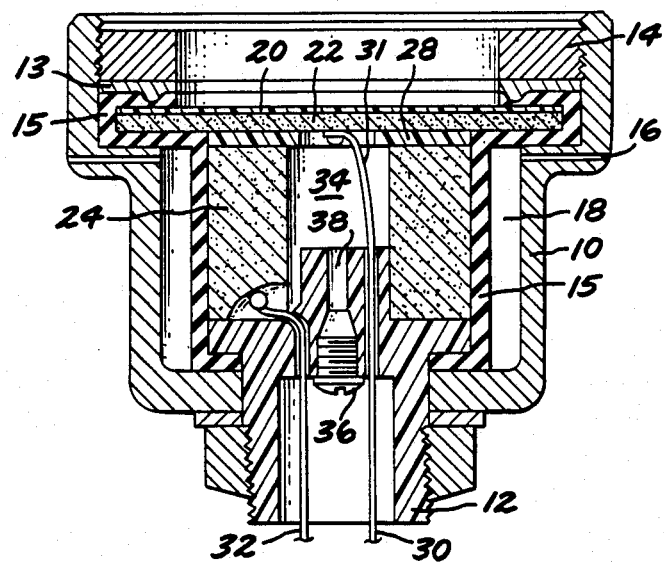
FIG. 1 is an axial sectional view of an oxygen sensor as provided pursuant to the present invention.

The sensor cell of FIG. 1 is a sensor cell and is essentially a copper-air battery cell. It includes an outer housing 10, preferably of polymeric material, and having an insulating bushing 12 at its lower end and an externally threaded plastic insert 14 at its upper end. Between the bushing 12 and the insert 14 are essential elements of the sensor. An impervious washer 13 is positioned between the upper portion of a bladder 15 and insert 14. This holds the top inwardly extending portion of bladder 15 against the outer portions of membrane 20 and defines the area of membrane 20 exposed to the atmosphere. An expansion bladder 15, of neoprene or other suitable rubber such as ethylene propylene rubber, laterally surrounds the essential components of the sensor and is positioned between these elements and the housing 10. The bladder 15 is spaced from the walls of the housing in the lower portion of the housing to permit its lateral expansion and vent holes 16 provide means by which gas pressure is equilibrated between the space 18, between the housing and the bladder, and the outside atmosphere. At the upper part of the essential elements of the sensor is a polymer membrane 20. The polymer membrane has the capacity to perfuse oxygen at a rate which is proportional to the partial pressure of oxygen in contact with the exterior surface of the membrane. Oxygen which is in contact with the exterior of the sensor passes through the membrane 20 and into contact with a sensing electrode 22.

The sensing electrode 22 is porous metal and it is gold-plated. The function of the gold on the sensing electrode is that of catalyzing the electro-reduction of oxygen. The extent of gold-plating must be sufficient to permit effective reduction of the oxygen and this degree of plating to achieve such effective reduction will be apparent to those skilled in the art. The porous sensing electrode makes contact with and has its pores wetted with potassium hydroxide electrolyte contained within the internal chamber of the sensor where a porous copper counter electrode 24 is located. The copper counter electrode is separated from the sensing electrode 22 by the insulating ring 28.

Figure 2:
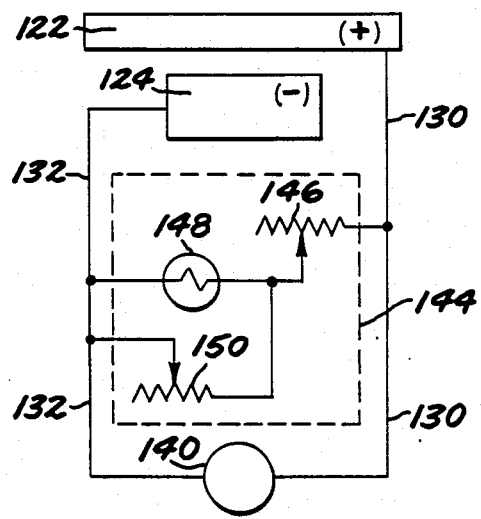
FIG. 2 is a schematic drawing of a sensing circuit as provided in connection with the present invention.

Suitable external circuitry such as is illustrated in and described with reference to FIG. 2 is provided between a sensing electrode 122 and a copper counter electrode 124. This circuitry includes connecting wires 130 and 132, a resistance network and a thermistor to compensate for temperature variations. The circuitry also includes a voltmeter in parallel with the network. Readings can be taken from the voltmeter of the voltage drop across the network resulting from the current flow between the sensing electrode 20 and the porous copper counter electrode 24 to provide an indication of the partial pressure of oxygen which is in contact with the exterior surface of the polymer membrane 20.

When oxygen diffuses through the polymer membrane and comes in contact with the sensing electrode, wetted with potassium hydroxide electrolyte, it is reduced electrochemically by electrons derived via the external wires and circuitry from the porous copper counter electrode 24. The counter electrode is concurrently oxidized electrochemically. At constant temperature the rate of these reactions, and hence the associated current flow, is proportional to the oxygen partial pressure in the environment being monitored. The current causes a potential drop across the resistance network connecting sensing electrode 22 and the porous copper counter electrode 24 which is measured by a voltmeter connected in parallel with the network. Wire 30 is connected through wire 31 to the sensing electrode and wire 32 is connected to the porous copper counter electrode 24.

The following are a few of the particulars of this prior art structure. The oxygen-diffusing membrane is a composite of fluorinated ethylene propylene polymer (FEP) and tetrafluoro ethylenepolymer (PTFE). See in this connection U.S. Pat. No. 3,616,411 as to alternative membranes.

The potassium hydroxide solution is a 25 weight % KOH electrolyte. The thickness of the oxygen-permeable membrane is typically about 0.025 mm. The sensing electrode is a disk with a 3.3 cm diameter and a 0.14 cm thickness. The counter electrode is a copper cylinder weighing 7.6 gm with a center bore. It has an outer diameter of 1.8 cm, an inner diameter of 0.8 cm and a length of 1.2 cm. The spacing between the sensing electrode and the counter electrode is of the order of one millimeter and is not critical.

When the sensor is exposed to air or oxygen, oxygen gas permeates through the membrane and is reduced at the sensing electrode. At the same time, the copper counter electrode is oxidized to copper oxide. The resulting current flows through an external resistor network and produces a voltage which is read on a voltmeter.

Typically, at a temperature of 75° F., the resistor network has a resistance of 110 ohms. Exposure of the sensor to air at 1 atmosphere pressure produces a current of about 400 microamperes ($\mu$a) and an output voltage of 44 millivolts across the resistor network. If the exposed surface of the membrane and the resistance values of the resistor network and the concentration of oxygen in air at constant temperature to which the sensor is exposed are all maintained as provided in prior art devices as specified above, the life of the prior art sensor is about 8800 hours. A sensing circuit suitable for use in connection with a sensor as provided pursuant to the present invention is illustrated schematically in FIG. 2.

The circuit is connected to sensing electrode 122 and counter electrode 124 by the wires 130 and 132. These elements of the circuit appear in FIG. 1 under the numerals 22, 24, 30 and 32 respectively.

A voltmeter 140 is connected in series with the sensing electrode 122 and counter electrode 124 through the wires 130 and 132 and gives a reading in millivolts of the voltage developed between the two electrodes when oxygen is being reduced at sensing electrode 122. The current can be calibrated in terms of partial pressure of oxygen to which sensor electrode 122 is exposed as is conventional with oxygen sensors. Some details of oxygen sensing equipment are described in the U.S. Pat. Nos. 3,149,921 and 3,616,411 which are incorporated herein by reference.

A thermistor/resistor network 144, enclosed by dashed lines in FIG. 2, is provided in parallel with a voltage meter 140 to permit a selected voltage to be developed between lines 130 and 132. The network consists of a variable resistor 146 in series with a thermistor 148, and a second variable resistor 150 in parallel with thermistor 148. The thermistor is incorporated in the known prior art circuit as illustrated to provide compensation for change in temperature of the sensor.

As indicated above for such sensors, typically at a temperature of 75° F., the resistor network has a resistance from line 130 to line 132 of 110 ohms. Output voltage is 44 millivolts on exposure of such sensor to air at 1 atmosphere pressure and a current of about 400 microamperes is generated.

The oxygen sensors as described above have been used for a number of years. Sensors as described above have been supplied to NASA for a period of over eight years.

A method for extending the useful life of an oxygen sensor as described herein is disclosed in the copending application of the same inventors Ser. No. 641,650 filed Aug. 17, 1984 and assigned to the same assignee as the subject application.

As explained in copending application Ser. No. 641,650 an apparatus such as that described above with reference to FIGS. 1 and 2 has been built and used commercially in connection with monitoring oxygen in space craft. The longer-lived sensor described and claimed in copending application Ser. No. 641,650 has been reduced to practice but has not been sold or used publicly or commercially or in space craft.

However it has been found with reference to this prior art apparatus of FIG. 1 and its operation that certain additional problems exist. One such problem is that described above and specifically the problem that the sensor output is unstable during start-up and in fact for a significant initial start-up time. This period is referred to as an initial break-in time. Extended break-in periods are required before stable and useful operation is achieved with a new sensor of the kind described with reference to FIGS. 1 and 2 above. The break-in procedure involves exposure to nitrogen at 25° C. for several weeks followed by exposure of the sensor to oxygen of various partial pressures for initial sensor calibration. Such exposure is done at different temperatures. During and after exposure of the sensor to these different environments, the sensor output is monitored and adjusted, and must ultimately comply with certain specifications regarding output sensitivity, output signal drift at constant oxygen pressure and output signal in nitrogen. The break-in, testing and calibration procedure occupies many weeks and exhausts a sometimes considerable fraction of the useful operating life of the sensor.

It is the object of our invention to provide a sensor with a stable output obtained after a much shorter break-in period. Such an improved sensor would allow for faster and simpler calibration and testing and would result in a much smaller fraction of its life being used up in the break-in period.

While we do not wish to be bound by the accuracy of our explanation of the phenomena, we offer an explanation here to assist those who seek to practice the present invention.

We believe that in order for the oxygen sensor to have suitably stable and reliable operation shortly after assembly, the copper counter electrode should have an initial small amount of oxide phase present and uniformly distributed through the counter electrode. In the initial absence of an oxide phase, the fresh copper counter electrode has only a superficial oxide on its surface, is very poorly characterized and its electrochemical potential is very poorly stabilized and can be significantly more electronegative than its equilibrium electrochemical potential value when phase oxide is present. The initial potential may be more negative by hundreds of millivolts. When the counter electrode is more electronegative than its equilibrium value any reading of electrical values taken from an oxygen sensor will be in error and will not accurately reflect the actual oxygen level of gas at the permeable membrane 20 of the device of FIG. 1.

There are a number of problems with breaking in the sensor after assembly. One is that the formation of phase oxide, which is essential for stable operation, tends to be non-uniform due to the non-uniform current density which is the result of the positioning of one end of the long cylindrical counter electrode with respect to the thin circular sensing electrode. The other is that it is uncertain as to just when the device is broken in. Erratic and inaccurate readings can persist for a significant time. Also the breaking in can use up a significant portion of the useful life of a sensor as described above with reference to FIGS. 1 and 2.

Further there is uncertainty introduced into the readings which are obtained and this uncertainty can persist because it may not be clear as to just when a sensor is fully broken in. Again without being bound by the explanation given we believe that in an actual break-in period of a sensor as described with reference to FIGS. 1 and 2, residual impurities are removed by oxidation and reduction, and oxide is formed on the copper counter electrode through electrochemical oxidation. After a certain amount of oxide has been formed on the copper counter electrode and after a certain distribution of oxide within the counter electrode has been achieved, the potential of the counter electrode reaches a stable equilibrium value.

Further we believe that when a small amount of solid phase oxide has formed and accumulated on the interior and exterior surface of the porous copper, of the order of ten to 100 monolayers, the value of the electrochemical potential will increase and will progressively approach a steady value. It is believed that when a sufficient number of monolayers have accumulated, prolonged stable operation is achieved indicating that the sensor has been "broken in" and the sensor can be applied to useful sensing of atmospheres.

In accordance with the present invention deliberate steps are taken before a counter electrode is incorporated in a working sensor to condition the counter electrode in order to stabilize the potential of the electrode.

One way in which such a copper counter electrode can be conditioned to stabilize its electrochemical potential is by taking deliberate steps to incorporate a small and finite amount of uniformly distributed cuprous oxide into the counter electrode structure. The copper counter electrode itself must be porous. In addition the cuprous oxide must be distributed through the porous copper counter electrode.

The actual incorporation of the cuprous oxide into the porous copper counter electrode may be accomplished in a variety of ways. In each case the amount of cuprous oxide is preferably between 0.1 and 5 percent by weight of the counter electrode.

Figure 3:
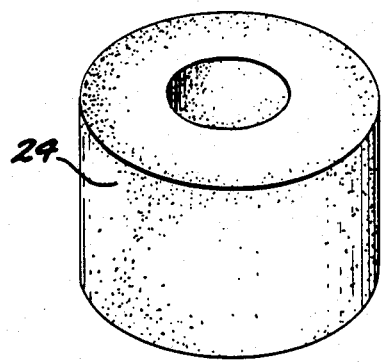
FIG. 3 is a perspective view of a counter electrode of the sensor of FIG. 1.

A first such way is by employing a mixture of copper and cuprous oxide powder in the initial formation of the porous copper counter electrode. The amount of oxide powder is small, amounting typically to between 0.1 and 5% by weight of the counter electrode. The metal and oxide powders are blended uniformly and then hot-pressed, followed by a final sintering step, both in a non-oxidizing environment, such as nitrogen. Hot-pressing is carried out in a cylindrical stainless steel mold of proper dimensions in a temperature range from 100° to 250° C. at pressures from 1000 to 5000 PSI for 5 minutes. Sintering is performed between 600° and 800° C. for 10 to 20 minutes. The choice of hot-pressing and sintering conditions determines the porosity of the finished counter electrode. The porosity is desired to be in the range of 15 to 30% by volume. A counter electrode in the form of a cylinder 40 having a toroid body 42 and a center bore 44 is illustrated in FIG. 3.

Another scheme by which such a copper counter electrode bearing a desirable level of cuprous oxide may be formed is by forming a porous copper counter electrode and oxidizing the interior and exterior surface of the counter electrode to form a predetermined small amount of cuprous oxide uniformly throughout the porous counter electrode.

The degree of oxidation which usefully conditions the counter electrode is that which will oxidize between 0.1% and 5% of the total weight of the counter electrode. Preferably about one percent of the total weight of metal of the counter electrode is oxidized to cuprous oxide.

The oxidation may be carried out by any convenient method such as in the gas phase or electrochemically.

Gas phase oxidation is performed at elevated temperature, that is, 100° to 200° C., in a mixture of nitrogen and oxygen, with the latter having a concentration well below that in air, to afford controlled and uniform oxidation. A partial pressure below about 0.1 atmosphere is preferred.

Preferably oxidation is carried out through an electrochemical mechanism because it affords the possibility to oxidize the counter electrode to a predetermined level by controlling the current and the time of oxidation. Electrochemical oxidation is carried out prior to sensor assembly in a cylindrical cell, made of suitable plastic, filled with an aqueous electrolyte consisting of 25% by weight KOH. The copper counter electrode is positioned vertically in the center axis of the cell and fully surrounded by a cylindrically wound sheet metal electrode made, for example, of nickel sheet. The copper electrode is connected to the positive pole of a suitable constant current source and thereby becomes the anode of the cell. The nickel sheet cathode is uniformly spaced from the copper anode at a distance of 1 to 2 cm to avoid non-uniform current distribution. To effect uniform oxidation of the copper electrode to the extent of approximately 1%, a current of about 0.6 mA is applied for 48 hours. Larger currents for correspondingly shorter times may be used, but at a sacrifice of uniform oxidation. The cell electrolyte is carefully outgassed prior to use, and inert gas, such as purified nitrogen, is bubbled through the electrolyte during electrochemical oxidation. The cell is provided with a tightly fitting cover with a small escape hole for the nitrogen. Such precautions are taken to avoid the accumulation of impurities and carbon dioxide in the cell electrolyte.

Porous copper cylinders which are prepared as described above to have been 0.1 and 5% by weight of cuprous oxide, and which can serve as counter electrodes in an oxygen sensor cell with a substantially reduced or minimum break-in processing are referred to herein as preconditioned counter electrodes. This description is appropriate because the counter electrodes which are prepared to contain 0.1 to 5.0% by weight of cuprous oxide do not require the prolonged and time-consuming and manhour-consuming break-in processing of prior art oxygen sensors. The provision of such preconditioned counter electrodes greatly facilitates the use of oxygen sensors and greatly reduces the cost of installation and breaking in of such oxygen sensors.

Because the counter electrode is preconditioned as taught herein the oxygen sensor cell with which it is employed may be provided with the preconditioned counter electrode and then stored for later use at an appropriate time. After a period of storage the cell with its preconditioned counter electrode may be supplied with alkaline electrolyte to initiate its operation as an oxygen sensor cell. The break-in time of such a preconditioned cell is greatly reduced as compared to a prior art cell which does not contain such a preconditioned counter electrode.

A sensor of this invention may be prepared in a dry state and stored dry. Addition of the electrolyte after such storage will initiate the sensing function of the sensor. The dry storage is feasible because the device does not have a prolonged break-in operating period before reliable oxygen sensing can be achieved and reliable oxygen concentration level readings can be obtained. Such dry storage is another feature of the sensor of this invention not available in prior art sensors.

The device of FIG. 1 is adapted to use as a storable oxygen sensor. In order to provide the storable version of the device the counter electrode 24 must have cuprous oxide uniformly distributed throughout its porous structure as described above. Also the well 34 of the device must not contain the electrolyte connecting the sensing electrode 22 to the counter electrode 24.

When operation of a storable sensor is to be initiated the screw 36 is removed and the sensor reservoir 34 is filled with electrolyte through the electrolyte fill port 38. The addition of an electrolyte such as the 25% KOH initiates the sensing function of the sensor. The screw 36 is then replaced to prevent egress of the added electrolyte.

Because the counter electrode of a storable sensor has been preconditioned as described above to have a small amount of 0.1 to 5% by weight of cuprous oxide distributed through the porous counter electrode, the break-in time for such sensor to give reliable readings of sensed oxygen partial pressure is minimal.

What is claimed and sought to be protected by Letters Patent of the United States is as follows:

1. A method of forming a preconditioned oxygen sensor cell which comprises
providing a porous body of copper metal having a large surface area for its volume,
distributing through said body of copper a quantity of cuprous oxide to constitute 0.1 to 5.0 percent of the weight of the body of copper,
maintaining a level of porosity of said body of at least 15 percent by volume, and
disposing said porous body in an oxygen sensor cell.

2. The method of claim 1 in which the quantity of oxide is 1 percent.

3. A method of forming a preconditioned oxygen sensor cell which comprises
providing a porous copper counter electrode,
heating the counter electrode to a temperature between 100° and 200° C. in an atmosphere containing oxygen in an inert gas at a partial pressure well below that of air,
continuing the heating until the porous copper counter electrode contains between 0.1 and 5.0% by weight of cuprous oxide, and
installing the oxide-bearing counter electrode in an oxygen sensor cell.

4. The method of claim 3 wherein the oxide content is about 1% by weight.

5. The method of claim 3 wherein alkaline electrolyte is added to the cell to initiate its sensing.

6. The method of forming a preconditioned oxygen sensor cell which comprises
providing a copper powder to be sintered,
admixing with said powder between 0.1 and 5% by weight of cuprous oxide powder,
hot-pressing the mixed powders at a temperature between 100° and 250° C. at a pressure of 1000 to 5000 psi for a period of about five minutes,
sintering the hot pressed powder mixture at a temperature of 600° to 800° C. for a period of ten to twenty minutes and
incorporating the counter electrode so formed into an oxygen sensor cell.

7. The method of claim 6 in which an alkaline electrolyte is added to said cell.

8. A method of forming a preconditioned oxygen sensor cell which comprises
providing a porous copper counter electrode,
introducing the counter electrode into an electrochemical cell containing KOH solution,
surrounding the counter electrode in said cell by a cylindrically wound sheet metal electrode and spacing said sheet metal uniformly from the counter electrode by a distance of one to two centimeters,
connecting the counter electrode to the positive pole of a constant current source to make the counter electrode the anode of the electrochemical cell and connecting the sheet metal electrode as cathode of the electrochemical cell,
passing a current of less than one milliampere through the cell for a period of time to produce from 0.1 to 5 weight percent cuprous oxide uniformly on the counter electrode, and
inserting the oxide-bearing counter electrode into an oxygen sensing electrode.

9. The method of claim 8 wherein the oxide produced is 1 percent by weight of the counter electrode.

* * * * *